United States Patent
Jones et al.

(10) Patent No.: US 7,751,895 B2
(45) Date of Patent: Jul. 6, 2010

(54) TISSUE TREATMENT DEVICE AND METHOD

(75) Inventors: Jeffrey W. Jones, Robertson, WY (US); Ioana M. Rizoiu, San Clemente, CA (US); Hodel McRae, Laguna Beach, CA (US); Dmitri Boutoussov, Dana Point, CA (US)

(73) Assignee: Biolase Technology, Inc., Irvine, CA (US)

( * ) Notice: Subject to any disclaimer, the term of this patent is extended or adjusted under 35 U.S.C. 154(b) by 86 days.

(21) Appl. No.: 11/447,605

(22) Filed: Jun. 5, 2006

(65) Prior Publication Data

US 2007/0208404 A1    Sep. 6, 2007

Related U.S. Application Data

(60) Provisional application No. 60/687,256, filed on Jun. 3, 2005.

(51) Int. Cl.
*A61N 1/34* (2006.01)
(52) U.S. Cl. .......................................... 607/46; 607/48
(58) Field of Classification Search .................. 607/46, 607/48
See application file for complete search history.

(56) References Cited

U.S. PATENT DOCUMENTS

| | | | |
|---|---|---|---|
| 4,080,737 A | 3/1978 | Fleer | |
| 4,535,784 A * | 8/1985 | Rohlicek et al. | 600/548 |
| 5,024,236 A * | 6/1991 | Shapiro | 600/548 |
| 5,365,624 A | 11/1994 | Berns | |
| 5,578,060 A * | 11/1996 | Pohl et al. | 607/3 |
| 5,674,261 A * | 10/1997 | Smith | 607/46 |
| 5,995,873 A * | 11/1999 | Rhodes | 607/46 |
| 6,022,316 A | 2/2000 | Eppstein et al. | |
| 6,183,434 B1 | 2/2001 | Eppstein | |
| 6,397,860 B1 | 6/2002 | Hill, II | |
| 6,494,900 B1 * | 12/2002 | Salansky et al. | 607/89 |
| 6,527,716 B1 | 3/2003 | Eppstein | |
| 6,669,685 B1 | 12/2003 | Rizoiu et al. | |
| 6,853,863 B2 | 2/2005 | Carter et al. | |
| 7,144,248 B2 | 12/2006 | Irwin | |
| 7,167,752 B2 * | 1/2007 | Lin-Hendel | 607/46 |
| 2003/0100824 A1 | 5/2003 | Warren et al. | |
| 2003/0208245 A1 * | 11/2003 | Mahadevan-Jansen et al. | 607/48 |
| 2004/0191729 A1 | 9/2004 | Altshuler et al. | |

(Continued)

FOREIGN PATENT DOCUMENTS

WO    WO 97/07928    3/1997

OTHER PUBLICATIONS

International Search Report, WO 2006/032057 A3, Mar. 23, 2006.
International Search Report, WO 2005/070154 A3 Aug. 4, 2005.

(Continued)

*Primary Examiner*—Carl H. Layno
*Assistant Examiner*—Tammie K Heller
(74) *Attorney, Agent, or Firm*—Stout, Uxa, Buyan & Mullins, LLP (57) ABSTRACT

A device for imparting therapeutic doses to living tissue is disclosed. The device includes a planar carrier including or structured to adjustably accommodate a multitude of electrodes. Positions of the electrodes may be altered by a user during a treatment procedure involving the impartation of therapeutic doses to the living tissue.

12 Claims, 2 Drawing Sheets

U.S. PATENT DOCUMENTS

2006/0085052 A1    4/2006   Feuerstein et al.
2006/0195164 A1*   8/2006   Sondergaard et al. ......... 607/76
2007/0060984 A1    3/2007   Webb et al.
2008/0097564 A1*   4/2008   Lathrop ..................... 607/115

OTHER PUBLICATIONS

International Search Report, WO 2006/133065 A3 Dec. 14, 2006.
Written Opinion, PCT/US06/21691, Dec. 3, 2006.
International Preliminary Report on Patentability, PCT/US06/21691, Dec. 3, 2007.

* cited by examiner

TISSUE TREATMENT DEVICE AND METHOD

CROSS-REFERENCE TO RELATED APPLICATIONS

This application claims the benefit of U.S. Provisional Application No. 60/687,256, filed Jun. 3, 2005 and entitled TISSUE TREATMENT DEVICE AND METHOD, the entire contents of all which are hereby incorporated by reference.

BACKGROUND OF THE INVENTION

Various tissue treatment devices have existed in the prior art, including electromagnetic energy emitting devices having or used with electrode elements for facilitating treatments such as improved tissue structure, composition or physiology.

SUMMARY OF THE INVENTION

Carriers, such as a suction cups, putties, and panels, are coupled with electrodes for providing treatments to tissues in accordance with certain aspects of the present invention. The carriers may be used to provide detection, treatment and/or management of various conditions including wound healing, pain management, tissue discoloration, tissue inflammation or damage, tumors, and pain. One or more customizable therapeutic zones can include a surface topography comprising corrugations, protuberances, pits, or other surfaces known to those skilled in the art to be suitable for facilitating therapeutic treatments to tissues.

In accordance with one aspect of the present invention, a method for imparting therapeutic doses to living tissue comprises applying a pulsed signal to the living tissue through a plurality of electrodes disposed at different locations on the tissue; receiving a response signal from the living tissue; detecting one or more painful trigger points of the living tissue, based upon one or more of the pulsed signal and the response signal; and directing the therapeutic doses of energy into a vicinity of the one or more detected trigger points of the living tissue, using the plurality of electrodes.

A device for imparting therapeutic doses to living tissue in accordance with another aspect of the present invention comprises a planar carrier including or structured to adjustably accommodate a plurality of electrodes, wherein positions of the electrodes may be altered by a user during a treatment procedure involving the impartation of therapeutic doses to the living tissue.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112.

Any feature or combination of features described herein are included within the scope of the present invention provided that the features included in any such combination are not mutually inconsistent as will be apparent from the context, this specification, and the knowledge of one skilled in the art. In addition, any feature or combination of features may be specifically excluded from any embodiment of the present invention. For purposes of summarizing the present invention, certain aspects, advantages and novel features of the present invention are described. Of course, it is to be understood that not necessarily all such aspects, advantages or features will be embodied in any particular implementation of the present invention. Additional advantages and aspects of the present invention are apparent in the following detailed description and claims that follow.

DETAILED DESCRIPTION OF THE INVENTION

Reference will now be made in detail to exemplary embodiments of the invention, examples of which may be illustrated in any accompanying drawings. Wherever possible, the same or similar reference numbers may be used in such drawings and the description to refer to the same or like parts. It should be noted that such drawings may be in simplified form and not to precise scale. In reference to the disclosure herein, for purposes of convenience and clarity only, directional terms, such as, top, bottom, left, right, up, down, over, above, below, beneath, rear, and front, may be used with respect to any accompanying drawings. Such directional terms should not be construed to limit the scope of the invention in any manner.

Although the disclosure herein refers to certain illustrated embodiments, it is to be understood that these embodiments are presented by way of example and not by way of limitation. The intent of the following detailed description, although discussing exemplary embodiments, is to be construed to cover all modifications, alternatives, and equivalents of the embodiments as may fall within the spirit and scope of the invention as defined by the claims. It is to be understood and appreciated that the process steps and structures described or incorporated by reference herein do not cover a complete process flow for the implementations described herein. The present invention may be practiced in conjunction with various medical devices that are conventionally used in the art, and only so much of the commonly practiced method steps are included herein as are necessary to provide an understanding of the present invention.

Any feature or combination of features described herein are included within the scope of the present invention provided that the features included in any such combination are not mutually inconsistent as will be apparent from the context, this specification, and the knowledge of one of ordinary skill in the art.

Although the disclosure herein refers to the use of a device having customizable therapeutic zones for treating tissue (i.e., hard and soft) including, for example, methods for treating painful trigger points which methods may relate to, for example, treating pain in muscle tissue with low-level laser therapy, or to a mouthpiece device and method, the device and process of the present invention are not limited to such uses. Devices of the present invention may be used, or modified for use, for any medical purpose that may benefit from the application of electromagnetic radiation or other suitable treatment implementation on or within tissues of the body.

Figure 1A:
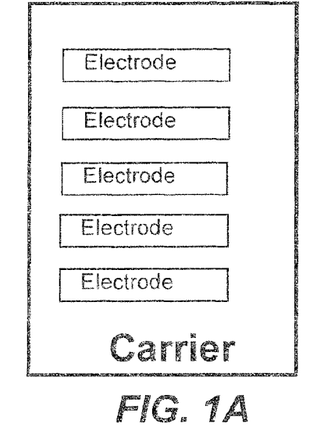
FIG. 1A is a block-diagram schematic of a carrier adjustably accommodating a plurality of electrodes.

Referring more particularly to FIG. 1A of the drawings, the device of the present invention generally can include a carrier comprising, or structured to adjustably accommodate, one or more electrodes (e.g., fiber optic output tips). In exemplary embodiments, the carrier may comprise an insert for a patient's mouth that fits to interior and/or exterior surfaces to, for example, fit the anatomy of the mouth, and/or a jaw contacting or mold-fitting device such as a jaw glove. In other embodiments, the carrier may comprise a pad (e.g., moldable pad) or other contacting device for fitting to or otherwise contacting external parts of the head or body. In accordance with an aspect of the invention, the carrier may be coupled with and/or may define a customizable therapeutic zone (which may be determined, at least in part, using, for example, a detector) that can be implemented using, for example, an electromagnetic radiation source. In other embodiments, the customizable therapeutic zone may be defined or detected using pressure sensors. One combination may comprise, for example, a pad or glove to fit on the face or pads to fit on the face or other body parts (e.g., back) to treat tissue regions such as painful trigger points. The one or more gloves or pads may be applied to the body internally and/or externally.

As an example, the block-diagram schematic of FIG. 1A shows a carrier for treating the temporomandibular joint (TMJ) that may comprise a jaw glove which is adapted to contact one or more of inside and outside tissues of the jaw. The jaw glove may comprise, for example, one or more of electromagnetic emitters, magnetic emitters, and/or fluid (e.g., air) pressure imparters, which may be placed to correspond with painful trigger points, meridians, or other therapeutic target muscle regions. In accordance with a preferred aspect of the present invention, the carrier is placed to correspond with tight-muscle or painful trigger points.

Figure 1B:
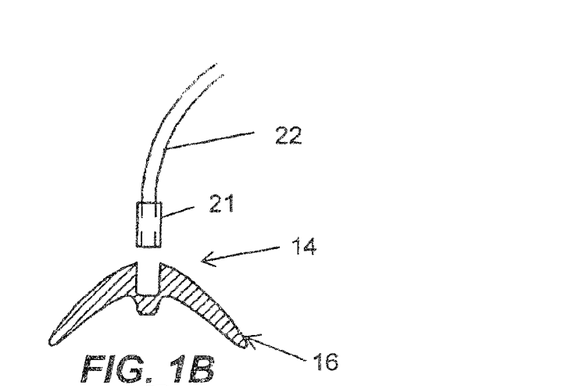
FIG. 1B is a cross-sectional view of a carrier comprising a suction-cup shape in accordance with an embodiment of the present invention.
Figure 1C:
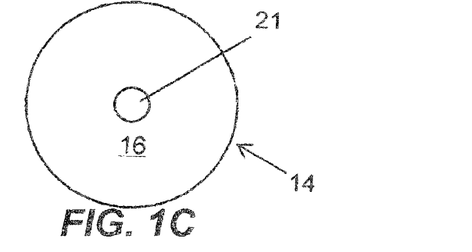
FIG. 1C is a top planar view of the configuration of FIG. 1B.
Figure 2A:
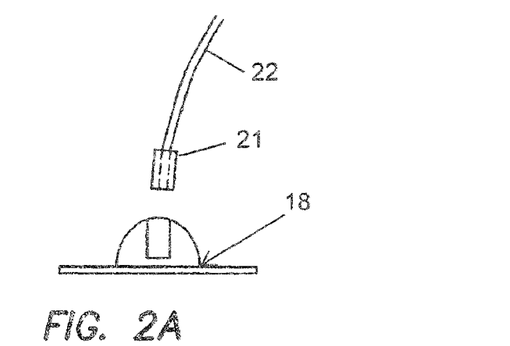
FIG. 2A is side-elevational view of a carrier comprising a planar material such as a flexible panel or an adhesive tape according to another embodiment of the present invention.
Figure 2B:
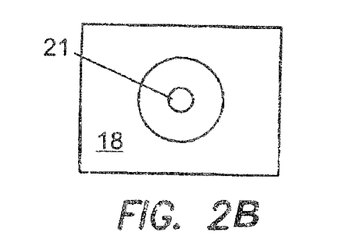
FIG. 2B is a top planar view of the construction of FIG. 2A.
Figure 3A:
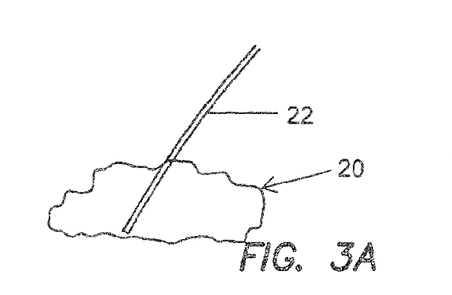
FIG. 3A is a partial cross-sectional view of a carrier comprising a moldable material according to yet another embodiment of the present invention.
Figure 3B:
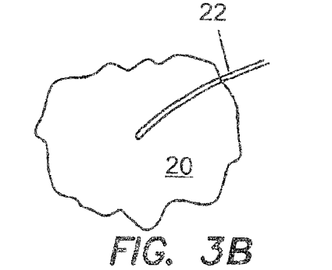
FIG. 3B is a top planar view of the construction of FIG. 3A.

According to certain implementations, the pad or pads may fit or be shapeable (e.g., moldable) to fit any part or parts of the body, such as treatment areas of the face or back. In one embodiment, a carrier can comprise the shape of a suction cup 16 and composition such as shown in FIG. 1B and the corresponding cross-sectional view of FIG. 1C and as known to those skilled in the art, a planar material such as a flexible panel and/or an adhesive tape 18 such as shown in FIG. 2A and the corresponding cross-sectional view of FIG. 2B, and/or one or more moldable materials 20 (e.g., a putty-like material) such as shown in FIG. 3A and the corresponding cross-sectional view of FIG. 3B. Any one or more of the carriers may comprise a known material, such as a medical grade plastic, rubber, or silicon rubber (e.g., a medical grade silicon rubber such as that sold by Dupont under the trademark Viton® or a neoprene material). Any of these materials may be transparent to the treatment radiation, may be disposable or sterilizable, and/or may comprise, for example, a diameter from about 5 to 20 cm. Furthermore, each of these carriers can comprise, as shown, a structure 21 for accommodating, orientating and holding a treatment radiation waveguide or conductor 22. The suction cup may comprise, for example, a pre-molded shape comprising advanced polymers, and the panel or tape may comprise a sheet of material having a construction (e.g., thickness, such as a thickness of 0.2 to 2.5 mm) and composition of the non-bandage portion of a wound cover such as a Band-Aid® wound cover.

Figures 4A, 4B, 4C, 5A, 5B, 5C:
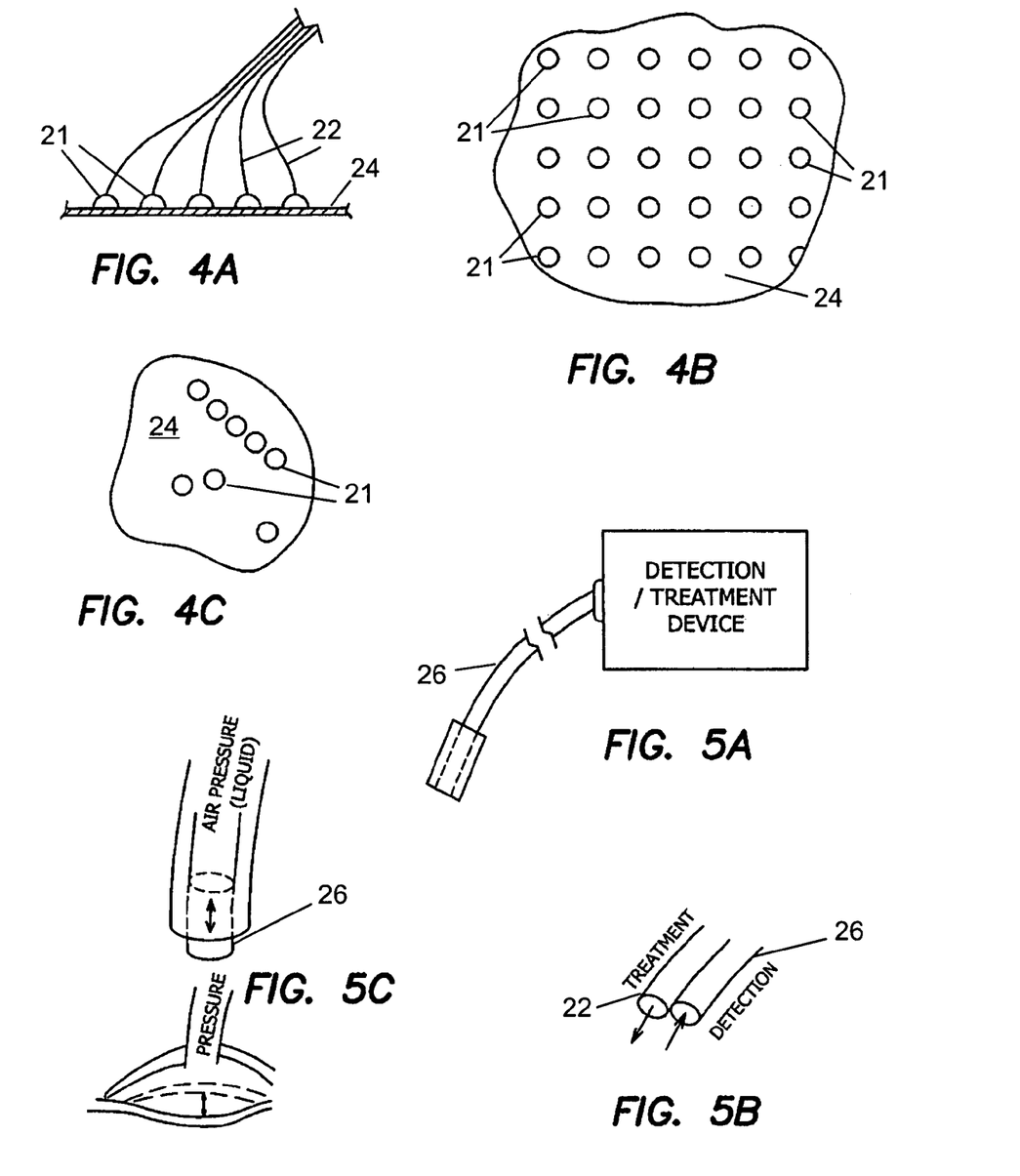
FIG. 4A is a side elevational view of a carrier separated into portions according to a further embodiment of the present invention.
FIG. 4B is a top planar view of a carrier separated into portions that may be defined at a time of manufacture of the carrier.
FIG. 4C is a top planar view of a carrier separated into portions that may be designed by a user based upon prior detected trigger-point locations or treatment locations of trigger points.
FIG. 5A illustrates a device for use in a procedure for detecting trigger points using fluid pressure in accordance with an aspect of the present invention.
FIG. 5B depicts a device for use in detecting trigger points using fluid pressure according to one implementation of the present invention.
FIG. 5C depicts a device for use in detecting trigger points using air pressure in accordance with another implementation of the present invention.

With reference to the cross-sectional view of FIG. 4A, and the two corresponding FIGS. 4B and 4C, a carrier 24 may be separated into portions (e.g., corresponding to different treatment regions and/or electrodes, wherein the portions may be defined at a time of manufacture of the carrier (cf. FIG. 4B) or designed by a user (cf. FIG. 4C) prior to use or in a follow-up procedure. In the latter case, for example, the placement of the electrodes may be based upon prior detected trigger-point locations or treatment locations of trigger points. The electrodes may be placed directly onto the skin or may be affixed to or otherwise placed upon a panel such as shown in FIGS. 4A and 4C, wherein, for example, the panel can optionally be transparent and the electrodes (e.g., electrodes such as shown in any one or more of FIGS. 1-3) can be removably coupled to the panel at various locations on the panel based upon various criteria such as trigger-point detection information and/or user input. The locations of the electrodes on the panel may be marked for subsequent positioning of the electrodes on the panel in a follow-up procedure, such as another painful trigger-point treatment procedure a few or more days later. In such an implementation of the invention, the positioning of the panel during the prior procedure should be determined, such as by triangulation with characteristics or features the user's body, to ensure accurate placement thereof in the follow-up procedure. In other embodiments, the transparent-panel carrier may comprise an active (e.g., powered) panel for performing one or more of the above tasks automatically or semi-automatically. For example, the panel may automatically record prior treatment data for a former treatment, such as the number and placement of various electrodes, and/or the signal characteristics of one or more (e.g., each) of the electrodes during the treatment procedure. The panel may also perform (e.g., automatically) detection protocols as described herein, before, during (e.g., at multiple times during), and/or after, treatment procedures for detecting locations, severities, and/or changes in conditions of painful trigger points. One or more changes in parameters (e.g., treatment doses or locations) of one or more of the electrodes can be recommended by the carrier (e.g., with LED indicators on the panel itself such as in an instructional mode of the panel, or on an external display, or by an audible message) based upon the detection protocols. In one example, at a time of the follow-up procedure, LED indicator symbols (e.g., small circles) may be displayed on the panel prior to the follow-up procedure to indicate to the user where the electrodes were placed in the former procedure as a recommendation to the user the electrodes be placed in the same location. In one embodiment, rather than (or in addition to) recommending changes in parameters (e.g., treatment doses) of one or more of the electrodes, the panel may control the electromagnetic source and delivery system to automatically adjust the parameter change(s). One embodiment may comprise the panel changing a transparency of itself between the electrode and the tissue being treated to thereby increase or decrease a dosage intensity, either continuously or intermittently, of treatment being delivered by the corresponding electrode to the tissue. In other embodiments implementing any of the above features, the carrier may comprise one or more of a tray, a band or insert, a tape or wrap, any known brace or support structure (e.g., braces), other similar structure, and combinations thereof.

The carrier may be used to provide detection, treatment and/or management of sundry conditions including, for example, wound healing, pain management, periodontal treatment, tooth discoloration, tissue inflammation or damage, tumors, and pain. The customizable therapeutic zone or zones may include a surface topography comprising one or more of corrugations, protuberances, pits, other surfaces known to those skilled in the art to be suitable for facilitating therapeutic treatments to tissues, and combinations thereof.

The electromagnetic radiation source may be any electromagnetic radiation source that emits radiation in any part of the electromagnetic region. In certain implementations, the electromagnetic radiation source can comprise one or more of an electrical potential or current, optical energy, sonic energy (e.g., vibrational or ultrasonic energy), and magnetism. Examples of electromagnetic radiation sources for emitting optical (e.g., light) energy can include, but are not limited to, one or more of heat emitting elements, LEDs, lasers or laser diodes, arc lamps, incandescent lamps, halogen lamps, neon lamps, and fluorescent sources. The electromagnetic radiation sources may emit electromagnetic radiation from, for example, ultraviolet to visible to infra-red light. In certain embodiments, electromagnetic radiation may be emitted at one or more wavelengths within the ranges of 400-650 nm and 650-1500 nm. In one embodiment, infra-red electromagnetic energy may be emitted, such as pulsed laser light having a wavelength of about 810 nm. The electromagnetic radiation may be emitted from a LaserSmile® system, manufactured by BioLase Technology, Inc. of Irvine, Calif. Other embodiments may comprise electromagnetic energy being emitted at wavelengths comprising one or more of about 810 nm, about 915 nm, about 935 nm, about 960 nm, about 980 nm and about 1064 nm. In other implementations, other infra-red spectral energy may be implemented.

The electromagnetic radiation sources, such as LEDs, may be provided at predetermined distances, for example, one LED per painful trigger point, or may be provided relatively close together. Positioning of the electromagnetic radiation sources may be performed at a time of manufacture or assembly of the carrier or may be performed after one or more detection steps, such as wherein electrodes are positioned on one or more moldable or otherwise configurable pads or gloves based for example on detection information. The particular spacings of electromagnetic radiation sources of a carrier, for example, can be determined and chosen to optimize a desired therapeutic treatment that is to be provided by the electromagnetic radiation via the carrier. According to an exemplary implementation of using LLLT to treat a painful trigger point, a contact-type fiber optic tip can be used to detect painful trigger points and deliver treatment doses of light. The fiber optic tip may comprise a diameter of about, for example, 0.1 to 10 mm, and in a particular implementation, of about 7 mm, and may deliver a power of about, for example, 0.01 W to 1 W.

In a detection mode, according to illustrative implementations, the power output of the source or stimulating beam may be any suitable level for, for example, 1 mW, and the return light for a reference target may have a power level that can be referred to as an expected or predetermined threshold level. A return of scattered light from a relaxed-muscle target back to a photo detector (e.g., a charge coupled diode or other known photo detector) may be about 10% of the power of the incident beam (e.g., may be about 0.1 mW). Accordingly, when the target is smooth or relaxed muscle the return light may have a power level that is a first amount (e.g., a predetermined percentage) above or below the predetermined threshold level, and when the target is knotted or tight muscle the return light may have a power level that is a second amount (e.g., a predetermined percentage) below the predetermined threshold level.

As an example, the predetermined threshold level may be set to number corresponding to a return signal of about 0.1 mW, the first amount may be set to an amount having about a plus or minus 5% deviation from the threshold level, and the second amount may be set to an amount smaller than the threshold level and having a deviation more than about 5% from the threshold level. According to such an example using a source signal of about 1 mW for an expected return signal of about 0.1 mW, a return signal within about 5% of the return signal can be interpreted (e.g., automatically interpreted by a circuit) to correspond to relaxed muscle and a return signal smaller than about 95% of the threshold level can be interpreted (e.g., automatically interpreted by a circuit) to correspond to tight muscle or a painful trigger point. In other instances, one or more of the first and second amounts may be, for example, zero. For example, in an example wherein the first amount is 2% and the second amount is 0%, for a source signal of about 1 mW and an expected return signal of about 0.1 mW, a return signal greater than the threshold level (e.g., the expected return signal) by up to about 2% can be interpreted to correspond to relaxed muscle and a return signal less than the threshold level can be interpreted (e.g., automatically interpreted by a circuit) to correspond to tight muscle or a painful trigger point.

In further implementations, a third amount can correspond to, for example, a lower limit for identification of a relaxed-muscle target and a fourth amount can correspond to, for example, a lower limit for identification of a tight-muscle or painful trigger-point target. One such embodiment corresponding to this implementation can comprise the first and second amounts being set, for example, to 0% and 2% again, and the third and fourth numbers being set, for example, to 0% and 10%, so that for a source signal of about 1 mW and an expected return signal of about 0.1 mW, a return signal greater than the threshold level by up to about 2% but not below the threshold level can be interpreted to correspond to relaxed muscle and a return signal less than the threshold level but not more than 10% less than the threshold level can be interpreted to correspond to tight muscle or a painful trigger point.

Other detection protocols can comprise a threshold level corresponding to an amount of scattered light returned from relaxed muscle wherein the second amount in these embodiments can correspond to an amount of scattered light returned from tight muscle or a painful trigger-point. Typically, the second amount may be about 0.01 mW less than the threshold level. For instance, a 1 mW source beam can be used in an embodiment wherein the reference target is set to be the relaxed muscle itself so that the predetermined threshold level corresponds to the amount of return light from the relaxed muscle (e.g., 0.1 mW). Here, scattered returned light from a tight-muscle or painful trigger-point target can have a power level that is a certain amount (e.g., a predetermined percentage) above the predetermined threshold level.

For any of the above and other detection implementations, detection of tight muscle or painful trigger-point areas generally will correspond to areas of tissue corresponding to decreases in a level of return light. In particular instances, the level of return light corresponding to tight tissue will be expected to be certain amounts less than levels of return light for areas of relaxed tissue, so that when such amounts are detected, or when relative reductions in the level of return light are detected, a decision may be made by circuitry (e.g., a microprocessor) of the present invention that an area of tight tissue or a painful trigger-point has been encountered. According to implementations using, for example, a source light of 1 mW and an expected level of returned light from relaxed tissue of 0.1 W, an anticipated level of returned light from tight muscle or painful trigger-point may be set to correspond to a reduction of the expected level (e.g., 0.1 mW) by a predetermined amount. This predetermined amount may range, for example, from about 0.001 mW to about 0.05 mW. In a particular example, the anticipated level of returned light, corresponding to a predetermined amount of about 0.01 mW, can be 0.11 mW.

Implementations utilizing an electromagnetic radiation source comprising or generating an electrical potential or current, in accordance with an aspect of the present invention, can comprise any known structure or technique for electrically discerning properties of tissue, such as muscle tissue. In a procedure for detecting painful trigger points in muscle, properties of the muscle can be detected and compared with reference parameters (e.g., properties of the muscle such as its impedance) that were generated during a detection procedure and/or before the detection procedure. In an exemplary implementation, the level of measured impedance for an area of tight tissue or a painful trigger-point will be expected to be less than the measured impedance for areas of relaxed tissue, so that when such lesser levels are detected, or when relative reductions in the level of impedance are detected, a decision may be made by circuitry (e.g., a microprocessor) of the present invention that an area of tight tissue or a painful trigger-point has been encountered. A technology for locating acupuncture trigger points, which are known as acupuncture energy points as distinguished from tight-muscle or painful trigger points, is the "Pointer Plus" by Texas Medical of Waxahachie, Tex., the entire contents of which are incorporated herein by reference. The specifications for this type of detector can consist of an output current of 0 to 40 mA, a frequency of about 10 Hz, a pulse width of about 240 us, and a continuous waveform.

In a procedure for detecting painful trigger points in muscle using fluid pressure, as illustrated in FIGS. 5A-5C, electrodes in the form of fluid pressure sensors 26 can be used to detect painful trigger points during and in between treatments wherein variances between pressure of tissues at various points of the tissue can be used to distinguish between relaxed muscle and painful trigger points. The pressure amounts to be applied, such as by application to a displaceable membrane that is deformed by positive pressure to impinge on the tissue, can be between ~0.1-2.5 Lbs/cm2. For some larger muscles the pressure may have to be increased to ~5 lbs/cm2. The distinguishing factor for discerning the painful pressure point or points will be pain or no pain reported by the patient. An off the shelf product that detects pressure using a metal gauge rather than fluid pressure is the algometer offered by Wagner instruments:

https://www.wagnerinstruments.com/wagnercatalog/xcart/home.php?cat=1.

According to a particular implementation of a treatment mode, the fiber optic tip 22 may deliver a power of about 0.56 W. With regard to one example, at the skin surface, the treatment light may comprise laser light, which has a wavelength of about 810 nm and which is output from the fiber optic tip at a power density of about 1.47 $W/cm^2$, wherein a spot size on the skin surface may have a diameter of about 7 mm with a corresponding spot size just beneath the skin surface (e.g., at a depth of about 6 mm beneath the skin surface) being about 3 to 4 times greater than the spot size at the skin surface (e.g., being about 28 mm). A dose of energy of about 23.6 $J/cm^2$ can be applied to a painful trigger point, or to each painful trigger point, for a period of about 60 seconds to thereby treat the painful trigger point or points. A net treatment delivered to each painful trigger point in one treatment can be about 33.5 Joules. Continuing with the example, at about 6 mm beneath the surface of the skin, the laser light may have a power density of about 0.39 $W/cm^2$, and a net treatment delivered to each painful trigger point at about 6 mm beneath the surface of the skin in one treatment can be about 9 Joules.

Any of the preceding forms of energy may be delivered using, for example, pulsed or continuous wave (CW) signals. In an exemplary implementation, at least one light source can be disposed on the carrier or routed to the carrier via, for example, a waveguide (e.g., fiber optic). In typical embodiments, the electromagnetic radiation source can be configured to emit one or more of coherent or non-coherent electromagnetic radiation (e.g., light) at a single or multiple wavelengths, and can comprise one or more of, for example, a light emitting diode, an optical fiber panel, an electrochemiluminescent material, an optical fiber bundle, and combinations thereof. One such embodiment can comprise the electromagnetic radiation source being configured to emit electromagnetic radiation at multiple wavelengths (e.g., corresponding to red and blue light), with the detector likewise being configured to detect the individual (or corresponding) wavelengths in the return signal and process (e.g., measure differences between) the wavelengths of the returned signal. For example, a source beam of red light will generate greater amounts of returned red light for oxygenated tissues; if an incident red source beam impinges on less-oxygenated tissue (e.g., having a greater content of blue color), more energy may be absorbed with less scattering and therefor a smaller return signal of red light. Ratios of returned red and blue light can be compared with the source beams of red and blue light to determine, for example, an oxygenation level of tissue. In modified embodiments, known techniques for detecting hemoglobin content in tissue, may also or alternatively be used to provide indications of, for example, an oxygenation level of tissue. An exemplary embodiment may comprise a source beam of about 1 mW and an expected return signal of scattered light of about 0.1 mW.

When multiple measurements of oxygenation levels of tissue are taken during a tissue treatment procedure, indications of whether the tissue treatment procedure is providing a desired effect (e.g., increasing circulation) on the target tissue can be generated. In modified embodiments, multiple measurements of oxygenation levels of tissue can be taken before, after and/or during a tissue treatment procedure. According to typical implementations, detected oxygenation levels can be compared with reference oxygenation levels (e.g., which are predetermined before the procedure and/or updated or generated during the procedure using one or more previous oxygenation-level measurements) and, based upon the comparison or comparisons, the tissue treatment procedure may be modified, either manually or automatically.

In particular instances, when oxygenation levels differing from a predetermined threshold (e.g., by more than about 10%) are detected, or when relative reductions in the level of detected oxygenation levels are detected (e.g., a second detected level differing from a prior detected level by more than about 15%), a decision may be made by circuitry (e.g., a microprocessor) and/or by a user that a treatment procedure may benefit from a modification or should be modified. The tissue treatment procedure may be augmented (e.g., by increasing one or more of an intensity, duration or other parameter of the tissue treatment procedure) or otherwise modified in response to an indication that the desired effect (e.g., enhanced circulation) is not progressing to the extent or in the manner desired. On the other hand, a tissue treatment procedure may be attenuated (e.g., by decreasing one or more of an intensity, duration or other parameter of the tissue treatment procedure) or otherwise modified in response to an indication that the desired effect (e.g., enhanced circulation) is progressing at a rate greater than expected.

According to one embodiment, a detected increase during a procedure of circulation in capillaries having relatively small diameters (e.g., external diameters of about 500 um to about 1000 um) of 15% or more, such as an increase of about 15% to about 60%, and, in certain implementations, of about 50% to about 60%, may be interpreted to correspond to a decision that the treatment procedure is progressing according to expectations. A detected increase during a procedure of circulation in capillaries having relatively large diameters (e.g., greater than about 1000 um) of about 1% to about 15%, may also be interpreted to correspond to a decision that the procedure is progressing according to expectations.

On the other hand, in some implementations, a detected increase during a procedure of circulation in capillaries having the relatively small diameters by an amount exceeding an upper limit, such as 80%, may be interpreted to correspond to a need or decision to attenuate or otherwise modify the treatment procedure, and a detected increase during a procedure of circulation in capillaries having the relatively large diameters by an amount exceeding an upper limit, such as about 15%, may be interpreted to correspond to a need or decision to attenuate or otherwise modify one or more aspects of the treatment procedure.

Likewise, in other implementations, a detected increase during a procedure of circulation in capillaries having the relatively small diameters by an amount less than a lower limit, such as about 15%, may be interpreted to correspond to a need or decision to augment or otherwise modify the treatment procedure, and a detected increase during a procedure of circulation in capillaries having the relatively large diameters by an amount less than a lower limit, such as about 1%, may be interpreted to correspond to a need or decision to augment or otherwise modify one or more aspects of the treatment procedure.

The electromagnetic radiation source may be powered by any suitable means that can cause electromagnetic radiation to be emitted from the source or sources. For example, the carrier may include one or more batteries, or an electrical power cord plugged into an electrical outlet. Batteries may be embedded in the carrier or may be disposed externally to the carrier. Tape, for example, may be provided with batteries placed within the tape and/or may be capable of being charged using a charging device.

The electromagnetic radiation source may comprise any known implementation for emitting treatment doses of electromagnetic energy (e.g., monochromatic or polychromatic radiation or energy) toward the tissue surface. According to a modified embodiment, the electromagnetic energy may be delivered, in whole or in part, as magnetism (e.g., from magnets within, or electrically activated within, the carrier) for implementing, for example, magnetic therapy. As used herein, the term "treatment doses" is intended to refer to quantities and concentrations of electromagnetic energy that are sufficient to, for example, cause one or more therapeutic or other intended effects (e.g., greater circulation or pain reduction) on or within the tissue of the tissue surface.

In certain embodiments, low-level light therapy (LLLT) or other energy-imparting therapy may be beneficially applied to tissues using (e.g., via electromagnetic energy transmitted from) the carrier. Treatment power densities may be relatively low, being similar, for example, to power densities used in treatments of, e.g., tennis elbow, temporomandibular joint, or tendonitis, and in representative embodiments having characteristics similar to or substantially the same as the above example implementing a power density at the surface of the tissue being treated of about 1.47 $W/cm^2$, a power density within the tissue of about 0.39 $W/cm^2$, a dose of energy delivered to a painful trigger point during a 60 second period of exposure of about 23.6 $J/cm^2$, and/or an energy of about 9 J within and about 33.5 J at the surface of the tissue being treated. As just one of many examples, in an embodiment wherein the carrier comprises an orthodontic structure, an electromagnetic radiation source may be incorporated to implement LLLT and reduce pain experienced by the patient from the orthodontic structure. The LLLT may originate from an electromagnetic radiation source disposed on or within the carrier as described herein and/or disposed separate and apart from the carrier, and may be implemented continuously or at predetermined periods of time (e.g., at times when the orthodontic structure is tightened) for predetermined durations.

The electromagnetic radiation may be used to treat painful trigger points that relate to, for example, pain or other conditions in tissue, such as muscle tissues or joints, disposed, for example, around a joint, in the face, in the head, in the wrist, in the elbow, or in the neck. A treatment for pain in a joint may comprise, for example, treatment of a temporomandibular joint condition. A treatment of pain in the wrist may comprise, for example, treatment of carpel tunnel. A treatment of pain in the arm may comprise, for example, treatment of tennis elbow. Treatment may comprise irradiation of one or more meridians or painful trigger points according to a detection, diagnosis and/or otherwise determined need of a patient.

The electromagnetic radiation treatment of tissue may comprise one or more of at least two exemplary methods. A first exemplary method may comprise irradiating a large area of tissue with electromagnetic radiation. A second exemplary method may comprise irradiating smaller areas, such as determined trigger points, with electromagnetic radiation through, for example, an optical fiber or a bundle of optical fibers according to a diagnosis and needs of the patient. A face glove may be placed on the face of the patient, for example, and the optical fibers attached to the face mask and configured to transmit the electromagnetic radiation to the trigger points adjacent the face glove.

The irradiation of trigger points through a bundle of fibers may allow several trigger points to be treated simultaneously or in accordance with a treatment timing pattern or protocol. The fibers may be attached to the skin via the carrier, which may comprise, for example, one or more of electrodes, suction, adhesives, pastes, gels, etc. The gels, pastes, adhesives, or other forms of attaching the fibers to the skin can allow attachment of the fibers to the skin or tissue at various locations and/or orientations.

The trigger points that are irradiated with electromagnetic radiation may be trigger points that are internal to the body and/or external to the body. If the trigger points are internal trigger points, irradiating the trigger points may comprise locating an electromagnetic radiation source inside the body and/or may comprise conducting the electromagnetic radiation from the electromagnetic radiation source to one or more internal trigger points through, for example, optical fibers or a bundle of optical fibers from an electromagnetic radiation source located, for example, external to the body. In certain embodiments, irradiating the trigger points may comprise irradiating both internal and external trigger points or may comprise irradiating at least one trigger point both internally and externally.

In particular embodiments, the source of electromagnetic radiation may comprise a laser. The laser source of electromagnetic radiation may comprise, for example, intense pulse light (IPL). In the case of intense pulse light, the intense pulse light may comprise a high-dose single pulse per time unit. In an alternative embodiment, the laser source may comprise low level laser light. The laser light may be filtered, for example. In an exemplary embodiment, the laser light therapy may comprise quick trigger laser therapy as is known to those having skill in the art. Laser treatment further may comprise, for example, low-power desensitization laser applications. In certain embodiments, a source of electromagnetic radiation for personal use may comprise a pointer-type laser and/or batteries as a power source. According to an aspect of the invention, the source of electromagnetic radiation (e.g., laser) may be taken home by the patient for treating, detecting or managing medical conditions in the home. Such low-power desensitization laser applications, or other therapeutic interventions involving application of electromagnetic radiation to tissue, may relate to or be based upon trigger point laser therapy information, patient data, or principles.

In accordance with one aspect, the carrier may comprise an integrated color meter to measure, for example, the color of the skin. In an exemplary embodiment, the intensity of the laser power may be reduced if the skin color that is measured with the color meter is relatively dark. Dark skin may absorb more light than light skin in certain embodiments. The power of the laser may be reduced by adjusting the wavelength and/or the intensity of light. Accordingly, treatment doses (e.g., doles of electromagnetic energy such as laser light) may be varied, depending on for example the diagnosis and the needs of the patient.

According to an aspect of the present invention, a method and device are provided for detecting trigger points in tissue, such as muscle. Trigger points can exist in connection with, for example, the presence of pain or discomfort in muscles or joints from inflammation or injury. For example, a dense knot may form or persist in muscle when there is or corresponding to pain or other condition(s) in the muscle. Detecting the dense knot in the muscle may comprise directing visible light, for example, a fluorescent light, on the muscle. Shining the light on the knot in the muscle may capture a difference between smooth muscle and knotted muscle, as a result of a scattering of light differential effect between tight or painful trigger-point muscle and smooth or relaxed muscle. Accordingly, detecting a trigger point in the muscle may comprise detecting a relative difference between the scattered light from a tight muscle and smooth or relaxed muscle.

In certain implementations wherein, for example, a light utilized for detecting the trigger points is variable between suitable intensity, spatial and/or time distributions, the method may comprise both detecting and treating one or more trigger points.

In accordance with one aspect of the invention, a phenomena to the effect that a microvoltage reading of a tight muscle can be different than a microvoltage reading of a relaxed muscle is utilized to facilitate tissue therapy treatments involving, for example, identification, detection and/or monitoring of trigger points or other tissue conditions. According to exemplary embodiments, microvoltage measurements can be conducted on tissues (e.g., muscle tissues) to detect, for example, tight, taught or otherwise afflicted or inflamed regions of the tissue, wherein, for example, microvoltage measurements of tissues of interest (e.g., trigger points) can yield a result that is detectably different than microvoltage measurements conducted on surrounding, adjacent or reference tissue (e.g., muscle) in a different location or condition such as a muscle in a relatively relaxed state. For example, detecting a dense knot in a muscle may comprise detecting a difference between microvoltages of a tight muscle and a relaxed muscle. As another example, detecting a dense knot in a muscle may comprise measuring the microvoltage of the muscle with a detector and comparing the measured microvoltage with a reference or expected microvoltage or set of microvoltages to thereby discern a condition, state or other property of the muscle. The process may be performed using a microprocessor, and the reference or expected microvoltage or set of microvoltages may be stored in a memory that is accessible to the microprocessor.

Pulse oximetry can comprise a non-invasive method of optically monitoring the percentage of hemoglobin that is saturated with oxygen. In accordance with one aspect of the present invention, the percentage of saturated hemoglobin in a tissue of interest is likely to vary, depending on the state or condition of that tissue. As embodied herein, detecting trigger points may comprise, for example, measuring the saturated hemoglobin percentages in tissues of interest with a pulse oximeter as a detection device. Detected differences in hemoglobin percentages in accordance with the present invention can be an indication of micro circulation in the tissue. For example, detecting an inflamed condition in a tissue (e.g., muscle) may comprise detecting a difference between saturated hemoglobin percentages of an inflamed tissue and a healthy tissue. As another example, detecting an inflammatory condition in a tissue (e.g., muscle) may comprise measuring a saturated hemoglobin percentage of the tissue using pulse oximetry and comparing the measured saturated hemoglobin percentage with a reference or expected saturated hemoglobin percentage or set of saturated hemoglobin percentages to thereby discern a condition, state or other property of the tissue such as a circulatory condition. The process may be performed using a microprocessor and the reference or expected saturated hemoglobin percentage or percentages may be stored in a memory that is accessible to the microprocessor. The pulse oximeter can thus provide real-time feedback on the state of a given tissue of interest before, during, or following application of therapeutic procedures on the tissue. Optical fibers, for example, may be connected to the tissue at various points on the body to simultaneously and/or intermittently monitor microcirculation at the various locations on the body.

In modified embodiments, detecting tissue regions (e.g., trigger points) that may benefit from therapeutic applications of electromagnetic radiation, via implementations of, for example, differential measurements of tissues or measurements of tissues and comparisons of those measurements with stored (e.g., reference) values, can comprise discerning properties of the tissues including one or more of hemoglobin saturation percentages and microvoltages as discussed above alone or in combination with optical (e.g., light scattering), sonic (e.g., vibrational or ultrasonic), electrical impedance, current, gaseous (e.g., airborne molecules components) and magnetic properties of the tissues. Any of the preceding properties may be detected using, for example, pulsed or continuous wave (CW) signal formats.

According to exemplary embodiments, following detection of a tissue condition a treatment (e.g., LLLT) may be directed onto the tissue as previously described. The treatment may be preceded by one or more of (a) a prompt by an electronic input/output device (e.g., via a speaker and/or display of the device, which may be operatively coupled to the carrier) and (b) a confirmation or instructional input by the user. Alternatively, the treatment may be initiated (e.g., automatically), following the detection, without any prompt and/or user input.

In other embodiments, following detection, discernment or collection of information regarding conditions or locations of a tissue area of interest, iterative processes may be used to impart therapeutic treatments onto the tissue area of interest. For example, location information of a tissue condition may be collected and communicated to the user via an input/output device operatively coupled to the carrier, followed by the performance of treatments as discussed herein, followed by one or more repetitions of the preceding collection, communication, and treatment steps. In certain embodiments, following detection, discernment or collection of information regarding conditions or locations of a tissue area of interest, iterative processes may be used to facilitate further detection, discernment or collection of information regarding the conditions or locations of the tissue area of interest. In a simple implementation, a speaker may issue an audible indication (e.g., beep) when a detector is passed over an area likely to contain a treatable condition or region (e.g., trigger point), thereby signaling such information to the user and/or signaling to the user that additional detection of the area may be warranted. According to various aspects, the detector implements one or more of impedance, potential, magnetic, sonic, light, visual and gas detection and/or comprises a wand movable by a hand of a user over tissue surfaces. An audible indication may signal to the user that additional detection of the area may be warranted in which case the user may move the wand back to a vicinity where the wand was positioned when the audible indication was issued. In certain embodiments, another audible indication may be issued when the wand is positioned back over the area and/or to signal, once again, to the user that additional detection of the area may be warranted in which case the user may again move the wand back over a vicinity where the wand was positioned when the most recent audible indication was issued.

According to one aspect of the present invention, an electronic input/output device operatively coupled to the carrier can be configured to provide an indication (e.g., an audible or visual alphanumeric message or an alarm) that a treatable condition should be brought to the attention of a professional (e.g., a doctor or specialist). For example, a scale of threshold levels may be programmed into the electronic input/output device for providing guidance (e.g., via audible or visual tones and/or worded messages) to the user on whether a detected treatable condition may or should be treated by the user at home and/or whether the condition should be brought to the attention of a professional.

In embodiments utilizing a display, the display may be part of or further comprise (e.g., be interchangeable with) a makeup mirror. For example, a 2-sided rotatable panel may comprise a makeup mirror on a first side and the display on a second side. In embodiments utilizing a speaker and/or a display, the display may further or alternatively comprise a telephone and/or videophone functionality. Other embodiments utilizing a speaker and/or a display may be programmed to indicate user information such as a prerecorded voice segment or photo of a user. The additional functionality may comprise an ability to play audio and/or visual information, such as vocabulary or foreign language lessons, music, news, or other prerecorded or real-time content.

In certain embodiments, content may be recorded into the electronic input/output device by the user (e.g., in the form of a memo recorded by the user the preceding evening), and in other implementations playback of the content may be performed according to a duration set by a user-defined timer. For example, in one instance language lessons may be played by the device for a predetermined or user-selected period (e.g., 2 minutes) with each use of the device, whereby the user may endeavor to perform a therapeutic treatment procedure (e.g., wear the carrier to perform LLLT on a jaw) for the playback period (e.g., 2 minutes).

In certain embodiments, an electronic input/output device coupled to the carrier may be configured to interface (e.g., via wireless, USB, RJ11, RJ45, and other ports) with other computer components, such as personal digital assistants (PDAs), personal computers, handheld and other portable media playback devices, using communication protocols known to those skilled in the art, such as Internet, Ethernet, BlueTooth®, etc. Data concerning any of the above-discussed processes thus may by electronically transferred (e.g., via email) to and from the electronic input/output device. For instance, upon a determination that a treatable condition should be brought to the attention of a professional, the electronic input/output device can either automatically or under user control forward relevant information to the professional.

In addition to being configured to control, for example, one or more of any characteristic or functionality of the electromagnetic radiation source and/or detector, the electronic input/output device may be configured to further effectuate or optimize treatment protocols. For example, in a context of treating a condition by applying an energy-based therapy to a tissue, the input/output device may control parameters including, for example, one or more of light, wavelength, brightness, power, or duration of emission, wherein in one implementation such parameters may be programmed as presets or may be operated manually by the user.

The above-described embodiments have been provided by way of example, and the present invention is not limited to these examples. Multiple variations and modification to the disclosed embodiments will occur, to the extent not mutually exclusive, to those skilled in the art upon consideration of the foregoing description. Additionally, other combinations, omissions, substitutions and modifications will be apparent to the skilled artisan in view of the disclosure herein. Accordingly, it is intended that the present invention not be limited by the disclosed embodiments, but be defined by reference to the appended claims.

The invention claimed is:

1. A method for imparting a therapeutic dose of energy to living tissue, comprising:
   (a) affixing first, second and third electrodes to a carrier, which comprises one or more of a panel and a glove;
   (b) positioning the carrier with the first, second and third electrodes at and in contact with a location on the living tissue;
   (c) applying first, second and third pulsed signals to the living tissue through, respectively, without limitation to order, the first, second and third electrodes, each of the pulsed signals being applied automatically through a corresponding one of the first, second and third electrodes under control of a microprocessor;

(d) receiving, in any or no order, first, second and third return signals, issued from the living tissue, through, respectively, without limitation to order, the first, second and third electrodes;

(e) comparing a value of at least one measurable characteristic of the return signals from a first one of the electrodes with the same characteristic of other ones of the return signals;

(f) determining with the microprocessor a painful trigger point to underlie at least one treatment electrode of the first, second and third electrodes, the at least one treatment electrode being determined, and also being selected for delivery of the therapeutic dose of energy, by the microprocessor from the comparing;

(g) directing the therapeutic dose of energy through the selected treatment electrode into a vicinity of the painful trigger point of the living tissue, whereby an amount of the therapeutic dose delivered by the selected treatment electrode is greater than amounts of therapeutic doses delivered by other ones of the plurality of electrodes; and (h) automatically repeating (c)-(g), but not (b), one or more times.

2. The method as set forth in claim 1, wherein:
the return signals comprise one or more of a potential, impedance, current, and optical energy; and
the measurable characteristic is one or more of signal level, signal duration, power level and power density.

3. The method as set forth in claim 1, wherein the living tissue comprises soft tissue.

4. The method as set forth in claim 1, wherein the therapeutic dose of energy is directed into the painful trigger point.

5. The method as set forth in claim 1, wherein the therapeutic dose of energy comprises sonic energy.

6. The method as set forth in claim 5, wherein the therapeutic dose of sonic energy is delivered as at least one pulsed signal.

7. The method as set forth in claim 1, wherein the therapeutic dose of energy comprises a therapeutic dose of electromagnetic energy.

8. The method as set forth in claim 7, wherein the therapeutic dose of electromagnetic energy is delivered as at least one pulsed signal.

9. The method as set forth in claim 7, wherein the therapeutic dose of energy comprises a therapeutic dose of one or more of electrical potential or current, optical energy, sonic energy, and magnetism.

10. The method as set forth in claim 9, wherein the therapeutic dose of electromagnetic energy is delivered as at least one pulsed signal.

11. The method as set forth in claim 1, wherein the determining of a location of a painful trigger point occurs when the measurable characteristic of the response signal of the treatment electrode is less than a stored or reference value for the measurable characteristic.

12. The method as set forth in claim 1, wherein the measurable characteristic is an impedance and the microprocessor determines the location of a painful trigger point when the impedance discerned from the response signal of the treatment electrode is less than a stored or reference impedance.

* * * * *